US012758118B2

(12) United States Patent
Perez Azpeitia et al.

(10) Patent No.: US 12,758,118 B2
(45) Date of Patent: Oct. 13, 2026

(54) DEVICE FOR MEASURING THE CONCENTRATION OF GASES IN EXHALED AIR

(71) Applicant: EVERSENS, S.L., Pamplona (ES)

(72) Inventors: Juan Maria Perez Azpeitia, Pamplona (ES); Leyre Ruete Ibarrola, Pamplona (ES); Ane Botas Penin, Pamplona (ES); Aitor Esquiroz Olcoz, Pamplona (ES); David Martinez Larrea, Pamplona (ES); Oleg Pafik Filipchuk, Pamplona (ES)

(73) Assignee: EVERSENS, S.L., Pamplona (ES)

( * ) Notice: Subject to any disclaimer, the term of this patent is extended or adjusted under 35 U.S.C. 154(b) by 805 days.

(21) Appl. No.: 17/441,424

(22) PCT Filed: Mar. 13, 2020

(86) PCT No.: PCT/ES2020/070178
§ 371 (c)(1),
(2) Date: Sep. 21, 2021

(87) PCT Pub. No.: WO2020/193828
PCT Pub. Date: Oct. 1, 2020

(65) Prior Publication Data
US 2022/0167870 A1 Jun. 2, 2022

(30) Foreign Application Priority Data
Mar. 22, 2019 (ES) ............................... ES201930260

(51) Int. Cl.
*A61B 5/08* (2006.01)
*A61B 5/00* (2006.01)
*A61B 5/087* (2006.01)

(52) U.S. Cl.
CPC .............. *A61B 5/082* (2013.01); *A61B 5/087* (2013.01); *A61B 5/742* (2013.01)

(58) Field of Classification Search
CPC .......... A61B 5/082; A61B 5/087; A61B 5/742
See application file for complete search history.

(56) References Cited

U.S. PATENT DOCUMENTS 11,009,501 B2 * 5/2021 Arregui San Martin .................... G01N 33/0037
2006/0178592 A1 * 8/2006 Nason ................. A61B 5/0803 600/532

(Continued)

FOREIGN PATENT DOCUMENTS

ES 2579911 A1 * 8/2016 ........... G01N 33/497
WO 2018174182 A1 9/2018

OTHER PUBLICATIONS

International Search Report for Corresponding International Application No. PCT/ES2020/070178, 2 Pages, Jun. 3, 2020.

*Primary Examiner* — Justin Xu
*Assistant Examiner* — Jonathan M Haney
(74) *Attorney, Agent, or Firm* — LUCAS & MERCANTI, LLP

(57) ABSTRACT

A device for measuring gas concentration in exhaled air is provided having an inlet for exhaled air, another inlet for filtered ambient air, an air suction pump, a sensor to measure concentration of a gas in the exhaled air, valves to direct the air, a meter to measure the flow of exhaled air, a humidity stabiliser and an air exhaust, wherein the humidity stabiliser is arranged downstream of the first air inlet and upstream of the flow meter, such that all the elements of the device are protected against the humidity of the exhaled air, the device being suitable for performing several exhalations, especially repetitive and at high flows, in short periods of time.

7 Claims, 3 Drawing Sheets

(56) References Cited

U.S. PATENT DOCUMENTS

| | | | | |
|---|---|---|---|---|
| 2010/0170323 | A1 | 7/2010 | Lighton | |
| 2015/0216448 | A1* | 8/2015 | Lotan | A61B 5/6898<br>600/538 |
| 2017/0119280 | A1* | 5/2017 | Ahmad | A61B 5/0878 |
| 2019/0344032 | A1* | 11/2019 | McCormick | A61M 16/024 |
| 2020/0022618 | A1* | 1/2020 | Mcclung | A61B 5/0833 |

* cited by examiner

DEVICE FOR MEASURING THE CONCENTRATION OF GASES IN EXHALED AIR

CROSS REFERENCE TO RELATED APPLICATION

This Application is a 371 of PCT/ES2020/070178 filed on Mar. 13, 2020, which claims the benefit of Spanish Patent Application No. 201930260, filed Mar. 22, 2019, which are incorporated herein by reference.

TECHNICAL FIELD

The present invention is related to the analysis of the concentration of gases in the exhaled air of a human being, such as, for example, the concentration of nitric oxide (NO), and in particular it relates to a device that enables gas concentration to be measured at multiple exhalation flows.

STATE OF THE ART

The analysis of exhaled air is a non-invasive technique with which an image of the composition of the blood can be obtained, which enables conclusive diagnoses on different aspects of the patient to be obtained, mainly in relation to the prediction and control of asthma, although it can also be applied to the detection of lactose intolerance or other conditions. Specifically, the determination of gas concentration in exhaled air, such as, for example, exhaled nitric oxide (FE NO), is a non-invasive technique that provides information on eosinophilic inflammation of the airways, related to asthma disease.

Nitric oxide concentration can be measured with an air analysing device that enables the detection of an increase in nitric oxide concentration in the air exhaled by the patient and the determination, based on the increase in nitric oxide concentration, of whether there is any condition in the respiratory system.

The respiratory system is often mathematically modelled. The application of mathematical models in the medical field enables, in a relatively simple way, parameters of clinical relevance to be estimated. The models used to characterise the respiratory system are of variable complexity, since in addition to defining the respiratory system with different degrees of detail, the precision of the estimated variables is different.

To date, the available models are distinguished into two types: compartment and morphology models. Compartment models are those that take into account the simple geometry of the respiratory system. In other words, they do not take into account the aspects related to the physiology of the system. Two models are distinguished: the two-compartment model, which describes the lung in a very simple way, and the multi-compartment model, which, despite also being a very basic representation, is a more complete approach. Moreover, the morphology model is more complex since, taking into account the physiological processes, it is capable of mathematically defining all the changes that occur in the lungs in each respiration cycle.

The alveolar concentration reaches its steady state in exhalations, or manoeuvres, of holding the breath for more than 8-10 seconds. Therefore, the air that is convected to the mouth during exhalation is conditioned by the NO that diffuses from the airway, so that the following expression is obtained:

$$J_{awNO} = J'_{awNO} - D_{awNO} \cdot C_{NO}$$

$$J_{awNO} = D_{awNO}(C_{ANO} - C_{NO})$$

Wherein ONO is the Nitric Oxide concentration of the upper airways, $CA_{NO}$ is the alveolar NO concentration, $D_{awNO}$ the diffusion coefficient of NO in the airway, $J_{awNO}$ the diffusion flow of NO through the airway and $J'_{awNO}$ is the maximum NO flow through the airway.

Once these parameters are known, the two-compartment model can be used to predict the exhaled NO concentration profile for any exhalation flow using a relatively simple exponential equation:

$$C_{ENO} = C_{awNO} + (C_{ANO} - C_{awNO})\exp\left(\frac{-D_{awNO}}{\dot{V}_E}\right)$$

To date, no standardised protocol is available for estimating these values, so different methodologies have been analysed to estimate these independent flow parameters.

As a summary, the following table shows the different methodologies that can be followed to obtain said parameters. The estimation method that can be used for each model can be quickly appreciated therein, the number of measurements necessary to estimate the parameters, as well as the required range of flows and the type of approach or resolution that is given to the mathematical model.

| | | Estimated Parameters | | | | Flow |
|---|---|---|---|---|---|---|
| Method | | $J'_{awNO}$ | $D_{awNO}$ | $CA_{NO}$ | $C_{awNO}$ | requirements |
| Tsoukias & George | | X | | X | | 2 measurements between 100-500 ml/s |
| Pietropaoli | | X | | X | | 2 measurements between 100-500 ml/s |
| Quadratic Eckel method | | X | X | X | | 4 measurements between 10-300 ml/s |
| Silkoff | 2 flows | X | X | | X | 2 measurements between 15-50 ml/s |
| | 9 flows | X | X | X | X | 9 measurements between 4.2-1550 ml/s |
| HMA | | X | X | X | X | 3 measurements between 5-500 ml/s |
| Tsoukias SB | | X | X | X | X | Single measurement with changing flow from 6% to 1% of vital capacity per second |

The multi-flow NO measurement method requires a manoeuvre with a set number of patient exhalations at both low and higher flows.

The air analysing devices on the market have a series of established flows, which limits the ability to apply different models. The problem with this is that there is still no standardised mathematical method due to the absence of air analysers that allow them to be applied, and define the most suitable for general use in the field of application. That is, there is a need in the sector to reach a standardisation of the flows to be measured to obtain nitric oxide measurements and flow-dependent parameters in a repetitive and standardised way, seeing the relationship in the NO concentration levels with respect to the exhalation flow.

In addition, since the multi-flow measurement method requires several exhalations to be carried out inside the device in a short period of time and, especially at high flows, it entails a condensation problem in the pneumatic elements of the device (tubes, valves, flow meter, etc.) that may affect the operation thereof and the final result of the measurement.

Document ES2579911B2, of the same applicant as the present invention, shows a device for measuring gas concentration in exhaled air that has a first air inlet to introduce air exhaled by the patient into the device, a second air inlet with a filter to introduce filtered ambient air into the device, an air suction pump, a sensor to measure gas concentration in the air, a humidity stabiliser, a flow meter to measure the air flow exhaled by the patient, an air exhaust so that the user can maintain a constant exhalation flow, and a series of valves to direct the air flow.

The humidity stabiliser is arranged immediately upstream of the sensor and enables the humidity level to be within established limits for the correct operation of the sensor; however, the arrangement of the humidity stabiliser immediately upstream of the sensor causes all the elements of the pneumatic circuit located upstream of the humidity stabiliser to be unprotected, and very especially the flow meter that determines the air flow exhaled by the patient to be unprotected.

Accordingly, the device of document ES2579911B2 is suitable for measuring at pre-established flows and with non-repetitive exhalations, but when it is required to measure at multiple flows that require the performance of several exhalations, especially at high flows, the device is not suitable since condensation occurs inside the pneumatic circuit of the device that makes it impossible to have reliable measurements. This is essentially due to the fact that no appropriate relationship between the NO concentration level and the air flow exhaled by the patient can be established.

Therefore, a device for measuring gas concentration in exhaled air is required that can be used to perform measurements at multiple flows, and that can be therefore suitable for applying the most appropriate mathematical model of the respiratory system considered by the medical professional.

OBJECT OF THE INVENTION

The subject of the present invention is a device for measuring gas concentration in the air exhaled by a patient. The device has an improved structural configuration with respect to the devices of the state of the art that are used for the same purpose, avoiding the generation of condensations in the device when several repetitive exhalations are made in short periods of time at different flows, and therefore results in a device that can be used to apply different mathematical models of the respiratory system.

The device for measuring gas concentration in exhaled air comprises:

- a first air inlet to introduce air exhaled by a patient into the device,
- a second air inlet with a filter to introduce filtered ambient air into the device,
- an air suction pump,
- a sensor to measure gas concentration in the exhaled air,
- a first valve located downstream of the first air inlet and upstream of the sensor, and
- a second valve located downstream of the second air inlet and upstream of the sensor,
- a third valve located downstream of the sensor and upstream of an air outlet,
- a flow meter to measure the air flow exhaled by the patient,
- a humidity stabiliser to stabilise the humidity in the device, and an air exhaust.

According to the invention the humidity stabiliser is arranged downstream of the first air inlet and upstream of the flow meter. In this way, all the elements of the device are protected against the humidity of the air exhaled by the patient. Thus, the device is suitable for performing several exhalations, especially at high flows, and repetitive in short periods of time, thus being able to obtain reliable measurements and establish a suitable relationship between the gas concentration level with respect to the air flow exhaled by the patient.

The pump is adapted to maintain a constant air flow rate in the sensor. In this way, the air flow sucked in by the pump, and passing through the sensor, is always constant, regardless of the air flow exhaled by the patient. In this way, when the patient exhales air into the device, the constant air flow rate at which the pump suctions allows the resistance to exhalation to be invariable for the patient, and therefore helps to prevent the patient from changing their exhalation level.

The device additionally comprises a screen for representing the air flow exhaled by the patient, which is measured by the flow meter, and for representing the exhalation time. In this way, the patient can visualise at all times whether the air flow at which they are exhaling is within the required flow.

The device additionally comprises a control unit wherein gas concentration values measured by the sensor are stored when the exhalation flow is within predetermined values. In this way, the control unit only saves the gas concentration values that are within the necessary range for the application of the mathematical model selected by the medical professional, discarding the values that are not within the range.

Preferably the sensor is a nitric oxide sensor. Even more preferably the device additionally comprises a carbon monoxide sensor and/or a hydrogen sulphide (H2S) sensor. In the event of using more than one sensor, a pump is used for each sensor to keep the air flow constant for each sensor. Thus, there is a pump arranged upstream of each sensor.

In this way, the device allows the origin of nitric oxide from the different cavities of the human body to be evaluated, as well as carbon monoxide and hydrogen sulphide that can show a relationship with diseases of the respiratory system to be evaluated.

With all this, a device is obtained that enables gas concentration to be measured in multiple exhalation flows, making it suitable for applying different mathematical models of the respiratory system.

DETAILED DESCRIPTION OF THE INVENTION

In the sense of the present invention, in relation to a section of the air passage through the interior of the device, it is understood that a point is downstream, if it is located after the section considered, advancing in the direction of the air current, and it is understood that a point is upstream, if it is located after the section considered, advancing in the opposite direction to the air current. The direction of the air flow inside the device is represented by arrows and by a dotted line in the figures.

Figure 1:
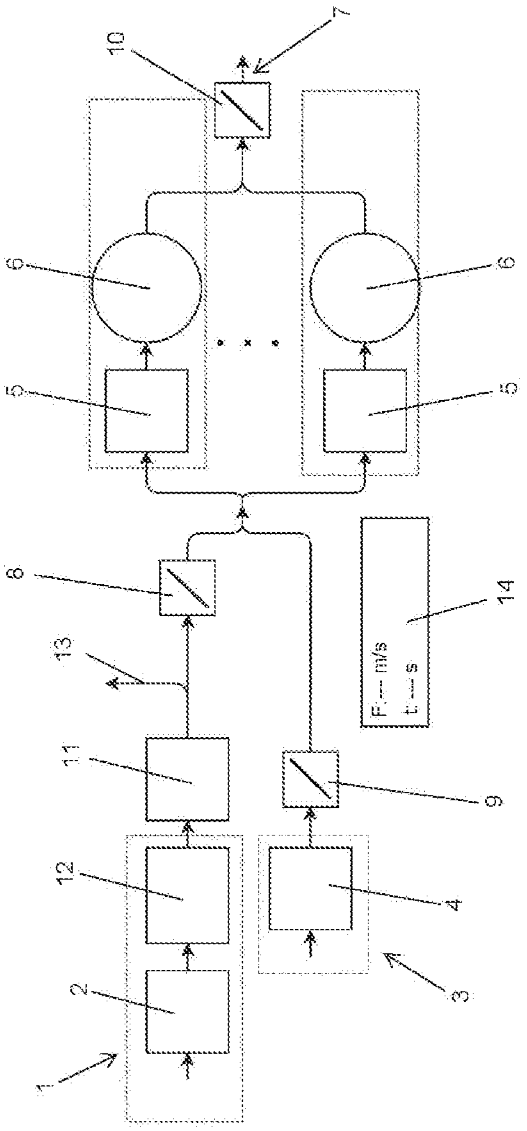
FIG. 1 shows a schematic view of the device for measuring gas concentration in exhaled air of the invention.

FIG. 1 shows a schematic view of the device for measuring gas concentration in exhaled air of the invention. The device comprises a first air inlet (1) having a nozzle (2) provided with an antibacterial filter through which the patient exhales air into the device and through which unfiltered ambient air can also be introduced inside the device. The device also has a second air inlet (3) with a filter (4) for a gas to be evaluated through which ambient air filtered from said gas to be evaluated is introduced. Preferably the gas to be evaluated is nitric oxide.

Downstream of the air inlets (1,3) there is at least one line with a pump (5) and a sensor (6) to measure gas concentration. Downstream of the sensor (6) an air outlet (7) is arranged through which air is evacuated to the outside of the device. FIG. 1 shows a device with more than one line provided with a pump and a sensor, although it may be possible to have as many lines as gases to be evaluated.

The device has valves (8, 9, 10) that are controlled during opening and closing by a control unit to direct the air inside the device.

The first valve (8) is located downstream of the first air inlet (1) and upstream of the sensor (6), the second valve (9) is located downstream of the second air inlet (3) and upstream of the sensor (6) and the third valve (10) is located downstream of the sensor (6) and upstream of the air outlet (7).

The valves (8,9,10) are solenoid valves that can switch between a status that allows air to pass therethrough and a status that obstructs the passage of air.

Downstream of the first air inlet (1) there is a flow meter (11) that determines the air flow exhaled by the patient, said information being used to determine the concentration of the gas to be evaluated in the exhaled air.

In the first air inlet (1) a humidity stabiliser (12) is arranged to stabilise the humidity in the device. Specifically, the humidity stabiliser (12) is arranged downstream of the first air inlet (1) and upstream of the flow meter (11). In this way, the stabiliser (12) is arranged in such a way that all the elements of the device arranged downstream of the first air inlet (1) are protected against moisture condensations that can be generated due to the exhalations of the patient.

Thus, the humidity stabiliser (12) is used to dry the air exhaled by the patient prior to entry into the device. Preferably the humidity stabiliser (12) is configured to reduce the humidity of the exhaled air to the humidity value of the ambient air.

The device has an air exhaust (13) that is located downstream of the first air inlet (1) and upstream of the pump (5). Preferably the air exhaust (13) is located downstream of the flow meter (11) and upstream of the pump (5).

The air exhaust (13) is a free air exhaust that has an air passage section that allows the patient to exhale comfortably up to the high exhalation flows required by the measurement technique, reducing the pressure sensation in mouth. Thus, the air exhaust (13) is a mechanical element that encourages part of the air flow to be directed towards the outside of the device, offering a comfortable resistance for the patient. The air exhaust (13) can be a solenoid valve or a fixed valve, or any other type of exhaust valve that enables the air to be restricted to reduce the pressure exerted by the user.

The device additionally comprises a screen (14) for representing the air flow exhaled by the patient and measured by the flow meter (11), as well as representing the exhalation time. The exhalation flow, the exhalation time, and the number of exhalations are selected by the medical professional according to the mathematical model to be used later. The representation of the flow on the screen (14) allows the patient to know the air flow at which they are exhaling, and therefore to be able to adjust their exhalation to the flow required for applying the selected mathematical model.

The pump (5) is adapted to maintain a constant air flow rate in the sensor (6), so that the pump (5) only allows the passage of a certain air flow through the sensor (6) which is subsequently directed towards the air outlet (7). Accordingly, when the patient exhales air into the device, the constant air flow rate at which the pump (5) suctions allows the resistance to exhalation to be invariable for the patient, and therefore helps to prevent the patient from changing his exhalation level due to changes in pressure that the device may deliver.

The pump (5) and the sensor (6) are arranged upstream of the third valve (10) and downstream of the first and second valves (8,9).

A sensor (6) has been provided for each type of gas to be evaluated. When a single gas needs to be analysed, it is generally nitric oxide, so a nitric oxide sensor is used, but when more gases other than nitric oxide need to be analysed, other sensors can be arranged, such as a carbon monoxide sensor, a hydrogen sulphide sensor, or others.

When several gases are analysed, as it is of interest to maintain the same flow level for each of the sensors (6), a pump is used for each of the sensors (6).

When using several sensors (6), a single third valve (10) located downstream of all sensors (6) can be used, or a third valve (10) located downstream of each sensor (6).

In the control unit of the device, concentration values of the gas measured by the sensor (6) are stored when the exhalation flow is within predetermined values. In other words, when the flow meter (11) detects that the exhalation flow of the patient is not within the parameters selected by the medical professional, a message is displayed on the screen (14) indicating that the flow is not correct and the values measured by the sensor (6) are disregarded. On the contrary, if the exhalation flow is within the selected parameters and the measurement is completed in the required exhalation time, the control unit calculates the average exhalation flow establishing a correction factor.

The measurement method is always based on taking relative measurements, calculating the difference between the concentration of the gas to be evaluated provided by the exhalation of the patient with respect to a reference baseline. Therefore, there is always a step of cleaning the inside of the device that establishes the reference level followed by a step of measuring the concentration of the gas in the air exhaled by the patient.

Figure 2:
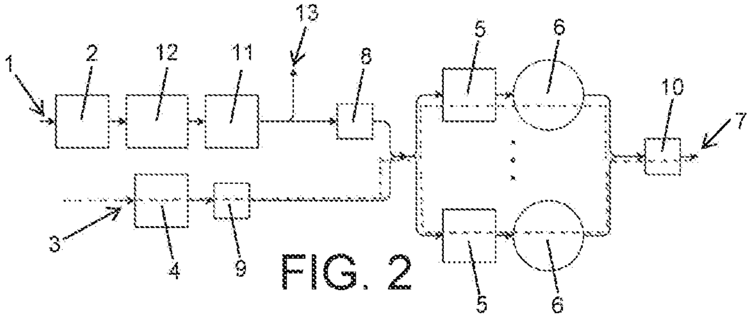
FIG. 2 shows the device of the previous figure operating according to a cleaning step.

FIG. 2 shows the cleaning step wherein the first valve (8) is closed while the second and third valves (9,10) are open, such that the pumps (5) suction air from the outside, causing it to pass through the filter (4) of the second air inlet (3) to direct it towards the sensors (6) and then to the air outlet (7). Thus, filtered ambient air that cleans the sensors (6) is introduced into the device, eliminating any remaining gas that could have remained in the sensors due to previous exhalations, thus establishing the reference baseline for the next measurement.

Figure 3:
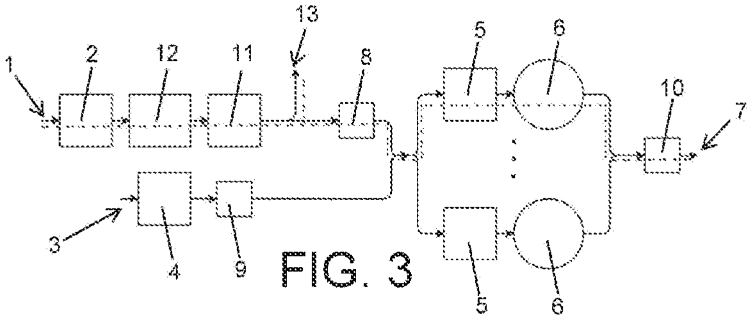
FIG. 3 shows the device of FIG. 1 operating according to an additional step for measuring the gas concentration in ambient air.

FIG. 3 shows an additional step for measuring gas concentration in ambient air. This measurement is not required, although it is advisable to perform it periodically, for example, at least once a day, since the variation of gas concentration in the ambient air can distort the measurements of the concentration of the gas in the air exhaled by the patient, being of interest to know said variations to be able to adjust the calculations if required.

Accordingly, in said additional step the second valve (9) is closed while the first and third valves (8,10) are open, such that the pumps (5) suck air in from the outside, causing it to pass through the first air inlet (1) to direct it towards the sensors (6) and then to the air outlet (7), and therefore measure gas concentration in the outside ambient air.

Figure 4:
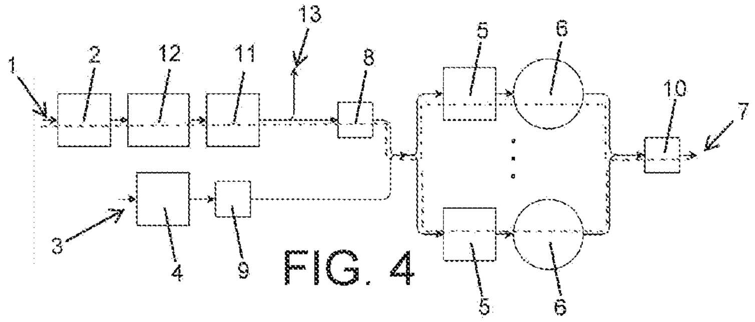
FIG. 4 shows the device of FIG. 1 operating according to a step of measuring gas concentration in the exhaled air.

FIG. 4 shows the step of measuring gas concentration in the air exhaled by the patient, wherein the second valve (9) is closed while the first and third valves (8,10) are open. Thus, the patient exhales air through the nozzle (2) of the first air inlet (1), wherein the exhaled air first passes through the humidity stabiliser (12), so that the exhaled air is dried by equating its humidity to the humidity of the ambient air.

Due to the air exhaust (13) and the constant suction flow rate of the pumps (5), the patient is able to comfortably exhale at the flow indicated on the screen (14). The exhaled flow is measured by the flow meter (11), which is not affected by possible condensations of humidity in the exhaled air due to the arrangement of the humidity stabiliser (12) upstream of the flow meter (11).

The pumps (5) absorb a part of the air exhaled by the patient causing a lower and constant flow through each sensor (6).

During the measurement of the gas concentration in the air exhaled by the patient, there is an instant of time when all the valves (8,9,10) are closed, leaving the sensors (6) in a sealed state during measuring in order to stabilise the response curve of the sensor (6), and thus be able to guarantee an appropriate measurement of gas concentration.

Figure 5:
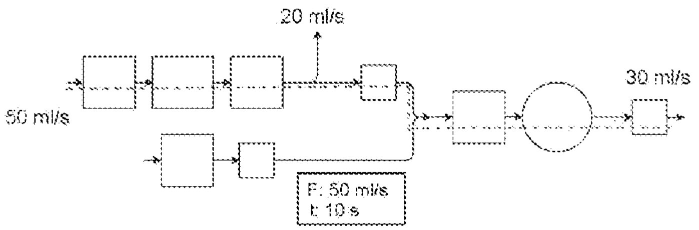
Figure 6:
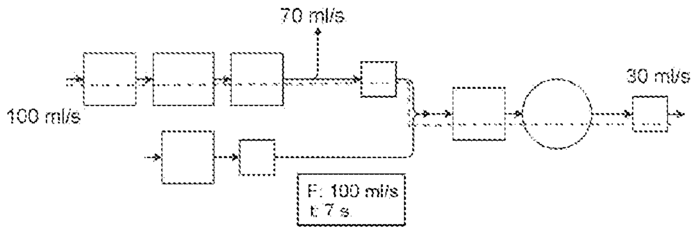
FIGS. 6 to 7 show the device of the invention operating according to three exhalation flows of 50 ml/s, 100 ml/s and 200 ml/s.
Figure 7:
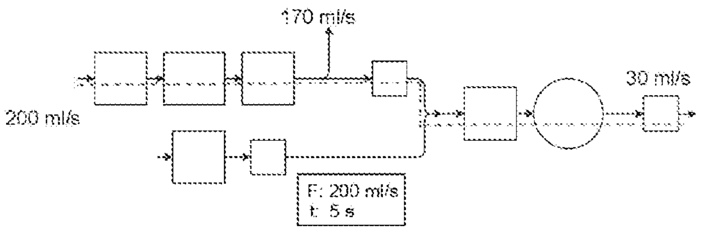

FIGS. 5 to 7 show three examples of measuring the concentration of the gas to be evaluated at three different exhalation air flows of 50 ml/s, 100 ml/s and 200 ml/s. (For the sake of clarity, the numerical references of the elements of the device are not represented in FIGS. 5 to 7, being the same as those of the previous FIGS. 1 to 4).

In all three cases the pump (5) is configured to generate a constant air flow rate through the sensor (6) of 30 m/s. Thus, in FIG. 5 the patient is required to exhale at a flow of 50 ml/s for 10 seconds, so that a flow rate of 20 ml/s comes out of the free exhaust, in FIG. 6 the patient is required to exhale at a flow of 100 ml/s for 7 seconds, so that a flow rate of 70 ml/s comes out of the free escape, and in FIG. 7 the patient is required to exhale at a flow of 200 ml/s for 5 seconds, so that a flow rate of 170 ml/s comes out through the free exhaust.

In all three cases, the exhalation flow at which the patient is exhaling and the exhalation time are represented on the screen for consultation by the patient and the medical professional.

The invention claimed is:

1. A device for measuring gas concentration in exhaled air comprising:

a first air inlet to introduce the exhaled air of a patient into the device, a second air inlet with a filter to introduce filtered ambient air into the device, an air suction pump, a sensor to measure the gas concentration in the exhaled air, a first valve located downstream of the first air inlet and upstream of the sensor, and a second valve located downstream of the second air inlet and upstream of the sensor, a third valve located downstream of the sensor and upstream of an air outlet, a flow meter to measure the air flow exhaled by the patient, a humidity stabiliser to stabilise a humidity in the device by drying the air flow exhaled by the patient, and a free air exhaust located downstream of the flow meter and upstream of the air suction pump, wherein the humidity stabiliser is arranged downstream of the first air inlet and upstream of the flow meter, thereby protecting elements of the device downstream of the first air inlet against moisture condensations, wherein the free air exhaust is arranged downstream of the flow meter, the first valve is downstream of the free air exhaust, and the air suction pump is downstream of the first valve, and wherein the air suction pump is arranged upstream of the sensor and adapted to maintain a constant air flow rate through the sensor when the patient introduces the exhaled air into the device.

2. The device according to claim 1, further comprising a screen for representing the air flow exhaled by the patient that is measured by the flow meter and for representing an exhalation time.

3. The device according to claim 1, wherein the air suction pump and the sensor are arranged upstream of the third valve and downstream of the first and second valves.

4. The device according to claim 1, further comprising a control unit wherein values of the gas concentration measured by the sensor are stored when the exhalation flow is within predetermined values.

5. The device according to claim 1, wherein the sensor is a nitric oxide sensor.

6. The device according to claim 5 further comprising a carbon monoxide sensor and/or a hydrogen sulphide sensor.

7. The device according to claim 1, wherein the humidity stabiliser reduces the humidity of the exhaled air to a humidity value of the ambient air.

* * * * *